United States Patent [19]

Fairfield

[11] Patent Number: 5,074,981
[45] Date of Patent: Dec. 24, 1991

[54] HIGH SPEED GEL ELECTROPHORESIS

[75] Inventor: Frederic R. Fairfield, Knoxville, Tenn.

[73] Assignee: The University of Tennessee Research Corporation, Knoxville, Tenn.

[21] Appl. No.: 343,991

[22] Filed: Apr. 26, 1989

[51] Int. Cl.$^5$ ...................... G01N 27/26; B01D 57/02
[52] U.S. Cl. ............................... 204/182.8; 204/299 R
[58] Field of Search ............ 204/299 R, 182.8, 182.9, 204/182.7, 180.1

[56]   References Cited

U.S. PATENT DOCUMENTS

| | | | |
|---|---|---|---|
| 3,047,489 | 7/1962 | Raymond | 204/299 |
| 3,371,027 | 2/1968 | LaPaglia et al. | 204/182.8 X |
| 3,407,133 | 10/1968 | Oliva et al. | 204/299 |
| 3,432,414 | 3/1969 | Rand | 204/299 R X |
| 3,499,833 | 3/1970 | Ferris et al. | 204/299 |
| 3,674,678 | 7/1972 | Post, Jr. et al. | 204/182.8 X |
| 3,751,357 | 8/1973 | Rains | 204/182.8 X |
| 3,873,433 | 3/1975 | Seidel et al. | 204/299 R X |
| 3,888,759 | 6/1975 | Elson et al. | 204/299 R |
| 3,902,987 | 9/1975 | Cawley | 204/299 |
| 3,915,827 | 10/1975 | Davies | 204/299 |
| 4,151,065 | 4/1979 | Kaplan et al. | 204/299 R |
| 4,194,963 | 3/1980 | Denckla | 204/299 |
| 4,234,400 | 11/1980 | Kaplan et al. | 204/180 G |
| 4,414,073 | 11/1983 | Iwata et al. | 204/299 R |
| 4,415,418 | 11/1983 | Turre et al. | 204/299 R X |
| 4,624,768 | 11/1986 | Yoshida et al. | 204/299 |
| 4,650,556 | 3/1987 | Hashiue et al. | 204/182 |
| 4,874,491 | 10/1989 | Stalberg | 204/182.8 |

FOREIGN PATENT DOCUMENTS 2089372 6/1982 United Kingdom ............ 204/299 R

OTHER PUBLICATIONS

Title: "Liquid Crystals", Author: James L. Fergason-Published in *Scientific American*, vol. 240, No. 2, pp. 77-85.

Primary Examiner—John Niebling
Assistant Examiner—John S. Starsiak, Jr.
Attorney, Agent, or Firm—Luedeka, Hodges, Neely & Graham

[57]   ABSTRACT

A method and apparatus for high speed gel electrophoresis employing elevated voltage values and relatively short time periods. There is disclosed a gel block having special geometry and including sample wells of triangular cross-section. Visual indication of the adherence of the procedure to temperature parameters is also provided for.

17 Claims, 5 Drawing Sheets

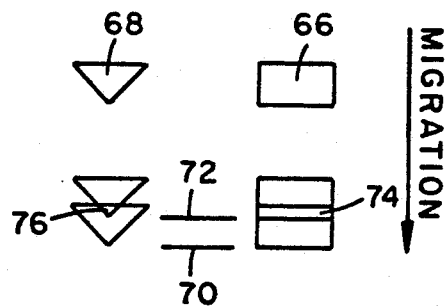
Fig.12
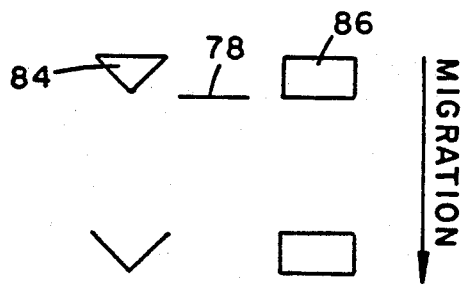
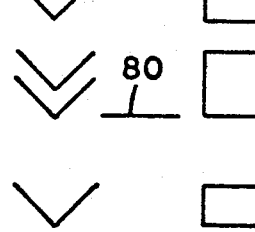
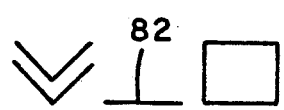
Fig.13
Fig.14

HIGH SPEED GEL ELECTROPHORESIS

FIELD OF THE INVENTION

The present invention relates to gel electrophoresis in which the components of a sample solution are separated by the application of a voltage across a supporting medium, i.e., a gel. In particular, this invention relates to methods and apparatus for electrophoretic separations at increased voltages applied over decreased time periods.

BACKGROUND OF THE INVENTION

Electrophoresis is used for the separation of ionic components in a sample solution. In the prior art, a sample solution is placed on or in a supporting medium (e.g. a piece of paper or block of gel) and a voltage is applied across the supporting medium. The charged components migrate through the supporting medium with a speed that is related to the charge on each component, the effective size of the component, and the applied voltage so that, over a given period of time, the components move different distances through the medium away from their common starting points.

The electrophoretic separation of biological compounds such as proteins or nucleic acids has become a widely used method for the identification and purification of individual components in a sample mixture. Present gel electrophoresis techniques require the use of voltages generally less than about 100 volts for time periods greater than about 30 minutes unless special and relatively expensive gels are employed. Even when using special gels, the time periods are greater than about 30 minutes.

Many biological compounds of interest consist of one component, such as a protein, bound to another component, such as a nucleic acid. Some of these compounds are bound together tenuously when removed from their natural biological systems and they may fall apart before the time required for the completion of the separation, purification and/or identification of the components using the present techniques of gel electrophoresis (i.e., greater than about 30 minutes).

The time required for the electrophoretic separation may be decreased by increasing the voltages used in the gel electrophoresis. Unfortunately, increasing the voltages also leads to an increase in the temperatures generated during separation. This increase in temperature may degrade the quality of the electrophoresis in at least two ways. First, since the medium used in gel electrophoresis may melt near or slightly above room temperature, gel electrophoresis techniques of the prior art at elevated voltages (i.e., greater than about 100V) may produce areas of the gel that may exceed the melting point of the gel. A sample loaded into a gel medium, such as an agarose gel, may become lost if parts of the gel become liquid and can no longer contain the sample.

Second, biological components, such as polypeptides, nucleic acids or other macromolecules may denature or significantly degrade at the elevated temperatures encountered when using high voltages for gel electrophoresis. Some of the denatured material may be renatured, but degraded components cannot, in general, be returned to their natural state for study or use. Both of these limitations to present gel electrophoresis techniques often limit the voltage to below about 100 V and the time periods of the separations to greater than about 30 minutes.

FIG. 2 shows a graphical representation of time and voltage conditions for conducting agarose gel electrophoresis. The area labeled 6 represents the conditions available for agarose gel electrophoresis using the techniques of the prior art. In general, the voltage is limited to less than 100 V and the time required to complete the separation exceeds 30 minutes.

Even when the gel electrophoresis is conducted within the limitations of the prior art techniques, the practitioner may still encounter problems with undesired temperature variations within the gel. During the course of preparation of the gel medium, it is possible that there may be areas of inhomogeneity in the final gel due to incomplete mixing of the gel material. While the electrophoresis is in progress, these areas of inhomogeneity may experience temperatures above that of the gel as a whole. Those areas of the gel may even melt. But, even if the temperature variation is not enough to melt the gel, the components of the sample solution may be exposed to temperatures that lead to denaturation and/or degradation. In either case, the sample components may not be recoverable or those recovered may not be the ones expected. It would be of great practical value to be able to continuously and conveniently monitor the temperature at various points throughout the gel. The prior art gel electrophoresis techniques do not provide the means necessary to do that.

The insufficiencies of the prior art techniques of gel electrophoresis limit the types of separations that may be performed. In addition, there may be some uncertainty with regard to the nature of the recovered materials when a separation is conducted at or near the limits of the present techniques.

Therefore, it is an object of the present invention to provide a method for rapidly and efficiently separating the components of a sample solution by gel electrophoresis.

It is another object of the present invention to provide an apparatus for rapid electrophoretic separation of the components of a sample solution.

It is another object to provide for enhanced resolution of the separation of sample components when subjected to a gel electrophoresis procedure.

It is a further object of the present invention to provide a means for monitoring the temperature of the mediums containing the sample before, after and/or during the completion of the electrophoretic separation.

SUMMARY OF THE INVENTION

In accordance with the present invention there is provided a method for electrophoretic separation of the components of a sample solution employing the steps of disposing the sample within a gel block and applying a voltage across the gel block sufficient to develop a voltage of about 30-120 volts per cm of length of the block at least in the area of the sample while maintaining the temperature of the gel below its melting point. In the preferred gel block, the sample is disposed in wells, each of which has a triangular cross-sectional geometry when viewed perpendicular to the direction of current flow through the gel block. The apex of the triangle is oriented in the direction of anticipated travel of selected sample components within the gel when subjected to the applied voltage. Further, in a preferred embodiment, the temperature of the gel block over at least that area thereof which is immediate to the sample, is visually indicated as by means of a planar liquid crystal thermometer. By the present method and apparatus, it has been found possible to effect excellent and definitive separations of multiple components of a sample within a time period that is 1/15 or less, of the time period required in the prior art devices when the current can partially flow between the electrodes along a path that does not include the gel block. Not only is this time savings of significance, but also it has been found that the resolution of the separation is substantially enhanced through the use of the present invention.

There is also provided an apparatus for the electrophoretic separation of the components of a sample solution. The apparatus is comprised of a gel block with a generally rectangular shape with its opposite ends of adjusted thicknesses. At least one sample well is formed into the gel block for receiving the sample solution. In the preferred embodiment of the invention, the sample wells have a triangular cross-sectional geometry with the apex of the triangle oriented in the anticipated direction of travel of selected sample components when the gel is subjected to the applied voltage. Provision is made to ensure that the only electrical path between the electrodes of the apparatus is through the gel which contains the sample material.

FIG. 12 is a representation, in plan view, of a portion of a gel block following electrophoretic separation of identical aliquots of a sample contained initially in separated sample wells, one of rectangular cross-section and the other of triangular cross-section in accordance with the present invention.

FIG. 13 is a representation, in plan view, of a portion of a gel following electrophoretic separation, in accordance with the present invention, of supercoiled plasmid DNA (pMK108) from other DNAs and RNAs present in a crude plasmid preparation.

FIG. 14 is a representation, in plan view, of a portion of a gel following electrophoretic separation, in accordance with the present invention, of identical aliquots of Hind III cut lambda DNA contained initially in separated sample wells, one of rectangular cross-section and the other of triangular cross-section.

GENERAL DESCRIPTION OF INVENTION

Figure 2:
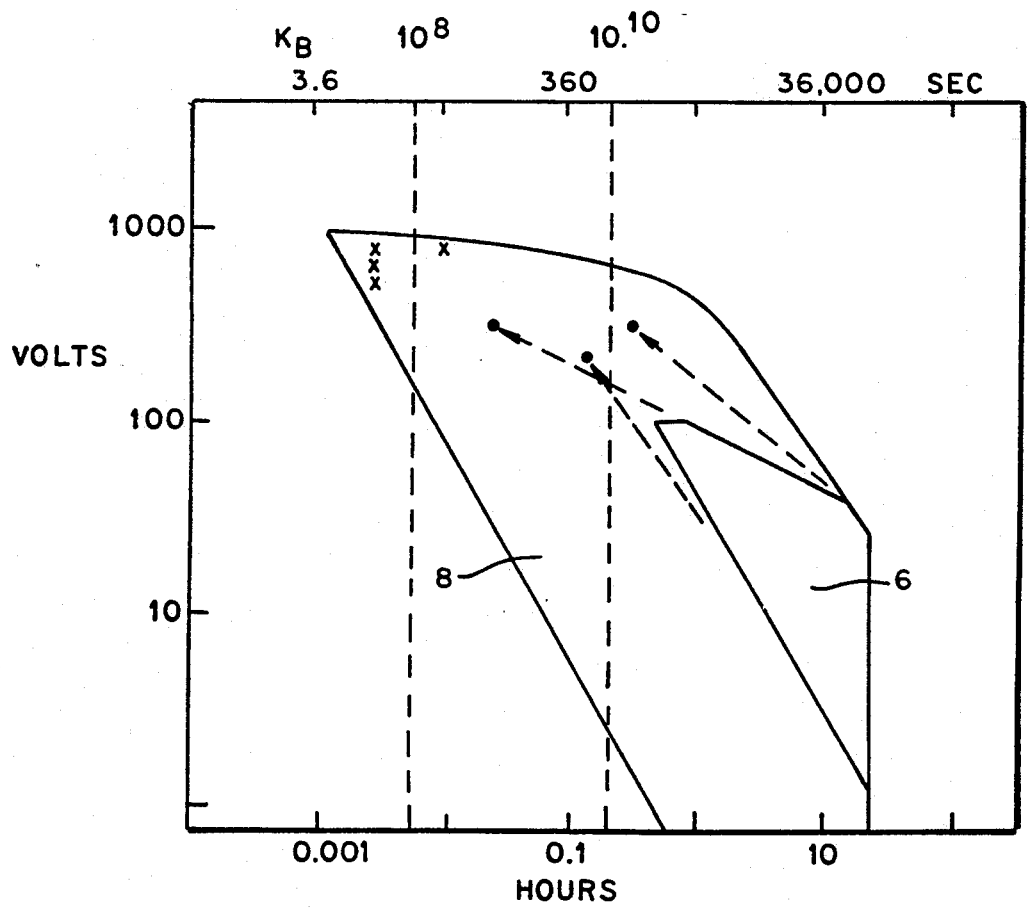
FIG. 2 is a graphical representation of various time and voltage conditions for conducting an agarose gel electrophoresis employing various features of the present invention and of the prior art.

FIG. 2 depicts the time and voltage conditions for conducting an agarose gel electrophoresis using the method of the present invention. In FIG. 2, the area of the graph that represents the techniques of the prior art, denoted 6, occupies a small portion of the conditions available using the method of the present invention, denoted 8, in FIG. 2.

Referring to the several FIGURES, and particularly to FIGS. 1, 3, 5, 8 and 10, there is illustrated an electrophoresis apparatus in accordance with the present invention including a preferred gel block 20 and sample wells 44 that allow the application of a voltage across the block of about 30-120 volts per cm of gel block length at least in the area of the sample, while maintaining a temperature that does not cause degradation or denaturation of the sample or damage to the gel.

Figure 3:
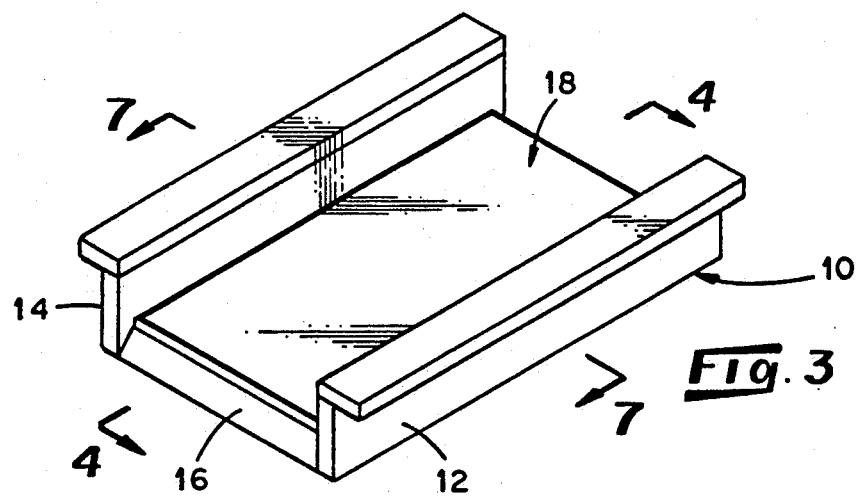
FIG. 3 is a schematic representation of one embodiment of a gel tray for use in the apparatus of the present invention.
Figure 6:
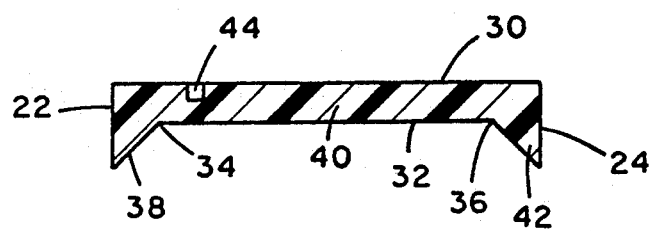
FIG. 6 is a sectional view of the gel block depicted in FIG. 5 and taken along the line 6—6 of FIG. 4.

A gel tray 10 is provided for holding the gel block 20. The gel block 20 may be preformed to be placed into the tray 10 or the gel block 20 may be formed in the tray 10. A liquid crystal thermometer 18 is mounted between the gel block 20 and the gel tray 10 with the thermometer 18 in thermal contact with the block 20. The preferred arrangement of the gel tray 10 and the liquid crystal thermometer 18 is shown in FIGS. 2, 3 and 6. An ice pack 15, for example, is shown as one embodiment for removing heat from the gel block prior to and during an electrophoretic separation procedure.

Figure 7:
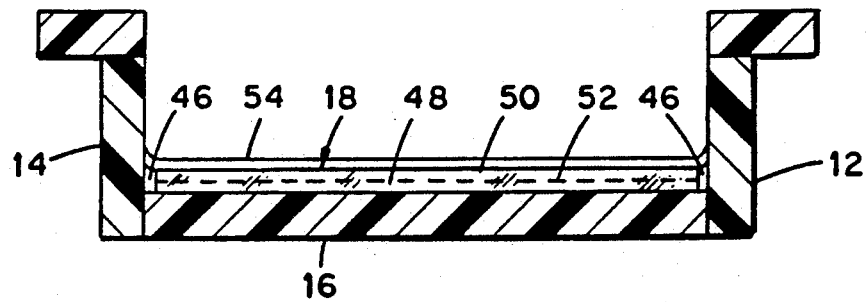
FIG. 7 is a enlarged sectional view of the gel tray depicted in FIG. 3 and taken along the line 7—7 of FIG. 3.
Figure 8:
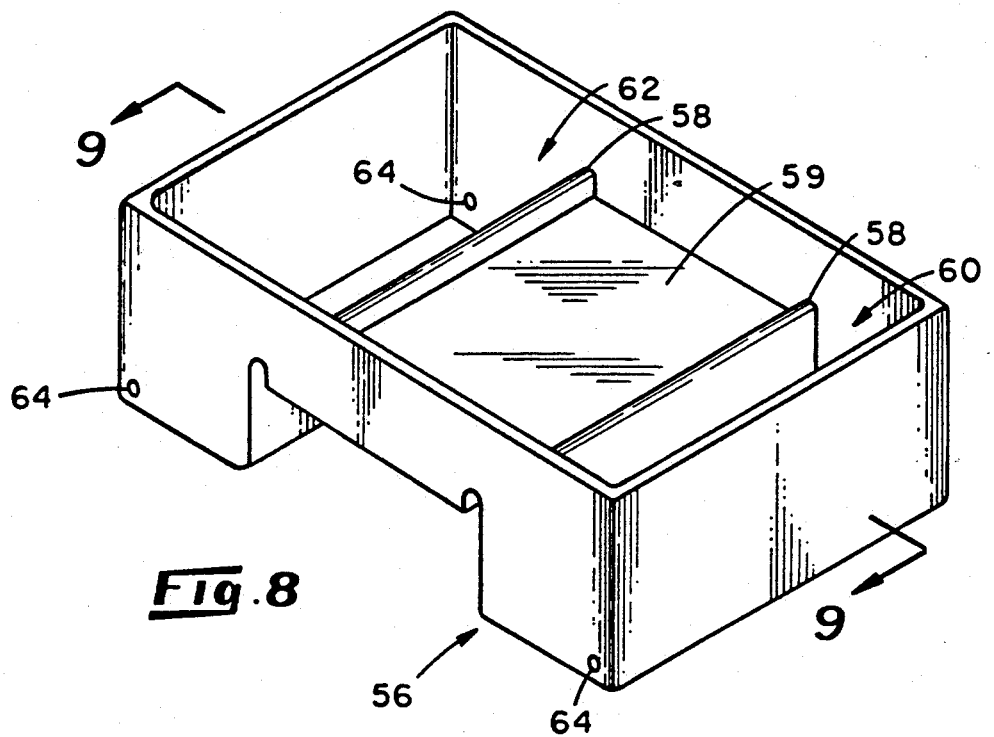
FIG. 8 is a schematic representation of one embodiment of a gel box for use in the apparatus of the present invention.
Figure 9:
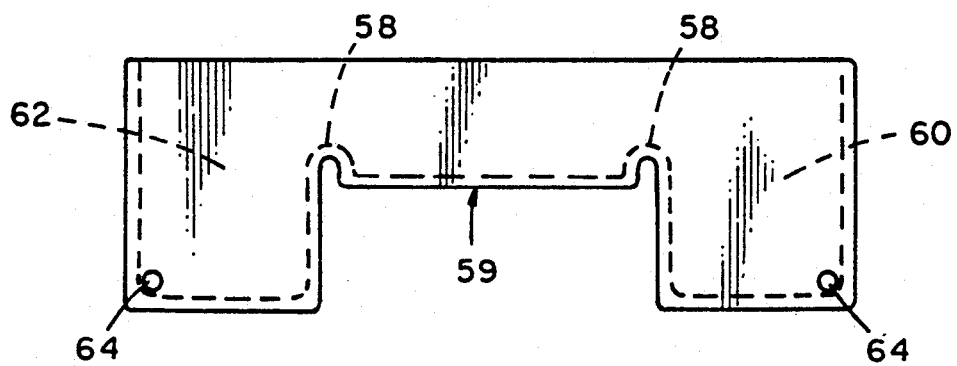
FIG. 9 is a sectional view of the gel box depicted in FIG. 8 and taken along the line 9—9 of FIG. 8.

There is also provided a gel box 56 for holding at least two buffer solutions in contact with opposite ends 22 and 24 of the gel block 20 without submerging the gel block 20 under buffer solution. Each buffer solution is contained in its own buffer well 60 and 62. Each buffer well has an electrode mounted in electrical contact with the particular buffer solution. An illustration of a preferred gel box is shown in FIGS. 7 and 8.

A means 67 for applying a voltage between electrodes 61 and 65 is also provided. When the apparatus is in use, the sample solution is placed into a sample well 44, a voltage from the electrical source 67 is applied to the electrodes, a voltage is developed across the gel block 20 and the components of the sample solution migrate through the gel 20. Sample components of a positive charge migrate toward the cathode and components of a negative charge migrate toward the anode.

Figure 5:
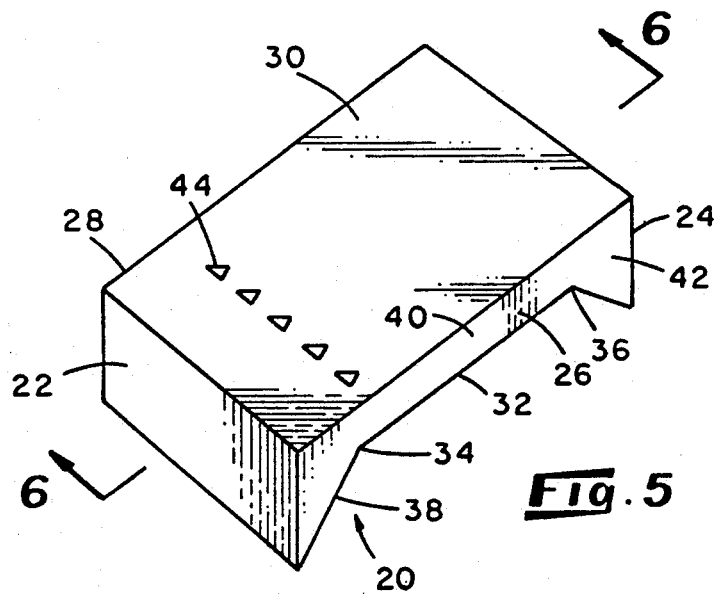
FIG. 5 is a schematic representation of one embodiment of a gel block as employed in the present invention and depicting preferred sample wells.

The gel block 20 of the present invention has a substantially flat first surface 30 and has a depth that differs at the ends 22 and 24 of the block which gives the block a special geometry. A longitudinal cross-section of the gel block as seen in FIG. 5 shows two generally wedge-shaped end portions 38 and 42 at opposite ends of the block and a generally rectangle-shaped middle portion 40 between the two end portions 38 and 42. The gel block 20 has a substantially uniform longitudinal cross-section across the entire width of the block 20.

The special geometry of the gel block 20 provides advantages over gel blocks of the prior art when the block 20 is subjected to the increased voltage values of the present invention. First, the middle portion 40 of the gel block has a relatively small constant depth that allows a heat flow path of minimum length during electrophoresis operations. The heat that is developed during electrophoresis may be rapidly removed from the block 20 by placing a heat sink in intimate contact with one surface 30 or 32 of the gel block 20. As well as requiring as thin a gel as possible to minimize the heat flow path, the middle portion 40 of the gel 20 should be sufficiently thick to provide for the electrophoresis of a usable sample solution size. In a preferred embodiment of the present invention, the thickness of the middle portion 40 of the gel block 20 is maintained at less than or about 2 mm. Such thickness allows the electrophoresis of between about 2 microliters and about 4 microliters of sample solution. Such thickness also provides for the heat flow away from the gel block necessary to prevent damage to the gel 20 or components of the sample solution under the elevated voltage values of the present invention.

Another advantage of the special geometry of the gel block 20 of the present invention is due to the wedge-shaped end portions 38 and 42 of the gel block 20. These end portions 38 and 42 extend from the flat first surface 30 of the gel block with a depth that is greater than the depth of the middle portion 40 of the block 20. The wedge-shaped end portions 38 and 42 may, therefore, be in substantial, intimate contact with the buffer solutions without requiring the submersion of the entire gel 20 in buffer. In the prior art, such submersion of the entire gel was a standard electrophoretic technique. In the present invention, the nonsubmersion of the gel block 20 provides that the only electrical contact between buffer solutions is through the gel block 20. In the prior art, the two buffer solutions were in electrical contact which allowed at least a portion of the current to be shunted around or over the gel 20. In such prior art devices, the buffer solution and the gel block both provided current flow paths between the electrodes. In the present invention, the inventor provides for the development of maximum voltage across the gel block by ensuring that essentially all the current flowing between the electrodes passes through the gel block. The wedge-shaped portions 38 and 40 also allow the buffer solutions to be in contact with a larger area of gel 20 than would be available using only the middle portion 40 of the gel 20. In a preferred embodiment, the middle portion 40 of the gel block 20 has a depth of less than about 2 mm while the wedge-shaped end portions 38 and 42 have a depth of greater than about 4 mm. The special geometry of the gel block 20 of the present invention has been found to allow the increased voltage values of the present invention which were not acceptable in the prior art due to degradation or damage to the components of the sample solution and/or the gel block.

The wedge-shaped end portions 38 and 42 of the gel block 20 in the present invention have an essentially trapezoidal geometry. A first side of the trapezoid is coincident with the flat first surface 30 of the gel block. Second and third sides are at right angles to the first side of the trapezoid and a fourth side is at an angle to the second and third sides. The second side of the trapezoid is coincident with one end 22 or 24 of the gel block, the third side is coincident with one end of the rectangle-shaped middle portion 40 and the fourth side is coincident with a second surface 32 of the gel block 20 that is opposed on the gel block 20 with respect to the first flat surface 30. In a preferred embodiment of the invention, the angle between the second side and the fourth side is about 45°, but a lesser acute angle between the second side and the fourth side of the trapezoid will give the desired special geometry. Therefore, the depth of the wedge-shaped portions 38 and 42 varies from about a maximum at a point coincident with the second side to a minimum at a point coincident with the third side.

The generally rectangle-shaped middle portion 40 of the longitudinal cross-section of the gel block 20 has a first side which is coincident with the flat first surface 30 of the block and a second side that is coincident with the second surface 32 of the gel block 20. Third and fourth sides of the middle portion are ends of the middle portion and are perpendicular to the first and second sides of the middle portion. Each of these ends is also coincident with the third side of the wedge-shaped end portions 38 and 42. The depth of the middle portion 40 is generally constant as measured from the first side 26 to the second side 28. The depth of the middle portion 40 is substantially the same as the minimum depth of the wedge-shaped portions 38 and 42.

In order to increase the resolution of (i.e., increase the ability to distinguish) the components in the sample solution, the sample wells 44 in a preferred embodiment of the invention have a substantially triangular cross-sectional geometry, as viewed at right angles to the flat first surface of the gel block 20, (i.e. perpendicular to the direction of current flow through the gel block) with the apex of the triangle being oriented in the expected direction of migration. In the prior art, sample wells were formed with a rectangular cross-section. The band produced by the migrating components of the sample from such prior art wells were of rectangular shape and tended to overlap. Triangular-shaped wells 44, on the other hand, have been found to produce V-shaped bands. The exact reason why the present apparatus produces V-shaped bands of migrating components is not known. However, it has been discovered that these bands are less likely to overlap and are more readily resolvable than are the bands seen in gel electrophoresis of the prior art. The preferred cross-section of a sample well defines an isosceles triangle, however other triangular geometries having an internal angle at their apex of between about 15 and about 120 degrees may be employed. Larger apex angles tend to cause the sample to migrate as in the prior art rectangular sample wells, however.

The gel tray 10 is used for holding the gel block 20. The ends of the base 16 of the tray 10, in a preferred embodiment, are beveled at an angle to the plane of the base 16 suitable to receive the ends of the gel block 20. A 45° angle is used in the preferred embodiment of the invention. The ends of the tray 10 are open and the sides 12 and 14 of the tray 10 are at right angles to the base 16. A liquid crystal thermometer 18 is mounted to the surface of the base 16. The thermometer 18 is mounted such that it will be in thermal contact with the gel block 20 when the gel block 20 is placed or formed in the tray 10 and, if desired, can be embedded in the gel. The thermometer 18 may be further composed of two or more liquid crystal thermometers 48 and 50 with different temperature ranges and mounted one atop another. In a preferred embodiment there is provided a means for determining which of the different temperature ranges is being indicated by the thermometers 48 and 50.

The gel tray 10 is placed onto a pedestal 59 in a gel box 56. The gel box 56 holds two buffer solutions in contact with the gel block 20. One buffer solution is in contact with one end 22 of the gel block 20 and the second buffer solution is in contact with the other end 24 of the gel block 20. Two electrodes are mounted in the gel box 56 so that they are in intimate contact with the two buffer solutions. The two buffer solutions are electrically connected to each other only through the gel block 20. The gel block 20 is not submerged in the buffer solutions and preferably no electrical path exists between the two buffer solutions other than through the gel block 20. There is also provided a means for applying a voltage between the two electrodes.

The apparatus is operated by placing a sample solution which has more than one ionized component into the sample wells 44. The gel block 20 is then placed in electrical contact with the buffer solutions. A voltage is applied to the two electrodes and developed across the gel 20. The components in the sample solution migrate through the gel block 20 at a rate which is dependent upon the charge and size of each component and the voltage across the gel block 20. Cooling techniques, such as a flat copper or aluminum plate having channels therein for the flow of a cooling liquid therethrough and disposed in good thermal transfer relationship to the gel block, will be recognized as acceptable. In some instances adequate heat removal can be accomplished by using a bag of ice water disposed on the exterior surface of the metal plate, as opposed to the use of coolant flowing through the plate. In a preferred embodiment, the flat plate is isolated electrically from the gel block as by a thin sheet (e.g. 0.05 mm thick) of high-density polyethylene. Such a sheet does not materially diminish heat transfer from the gel block to the flat copper plate.

This apparatus may be used to separate the components of a variety of biological sample solution but it is especially useful for separating nucleic acids. The gel block 20 may be composed of an agarose gel or other appropriate gel material. The gel block 20 is formed such that the depth of the block intermediate the end portions is of a magnitude to produce an efficient transfer of heat out of the gel block through at least one surface 30 or 32. Means for cooling the gel block 20 is applied to such surface 30 or 32 in order to remove heat from the gel block 20.

The present invention also discloses a method for the separation of the components of a sample solution employing gel electrophoresis. The method comprises the steps of disposing the sample solution in a gel block 20 and then positioning the gel block 20 between first and second buffer solutions. The buffer solutions are on opposite sides of and in electrical contact with the gel block 20. An electrically conductive path through the gel block 20 and between the buffer solutions is developed. The next step of the method is directing an electrical current through the gel block 20 via the buffer solutions for a time less than 30 minutes with the electrical current having a voltage value which develops between about 30 and about 120 volts per centimeter of length of the gel block 20.

In a preferred embodiment with an agarose gel, the voltage and the time period may be related such that the combination of the two is between about the limits given by the equations:

$$E = 0.5 t^{-1.1},\quad \text{Eq.1}$$

$$E = 500 t^{-1}, \text{ and} \quad \text{Eq.2}$$

$$E = 500 t^{-0.1}, \quad \text{Eq.3}$$

where E is the voltage in volts across the gel block and t is the time period in hours. This relationship is shown in FIG. 2 which is a graphical representation of the representative conditions for conducting an agarose gel electrophoresis employing the concepts of the present invention. It will be recognized from FIG. 2 that the present invention is useful over the ranges of time and voltages employed in the prior art, (denoted 6 in FIG. 2) but represents a significant improvement over the prior art in that the present invention provides for excellent electrophoretic separations at combinations of shorter times and higher voltages (denoted 8 in FIG. 2) than has heretofore been possible.

DETAILED DESCRIPTION OF THE DRAWINGS

Figure 4:
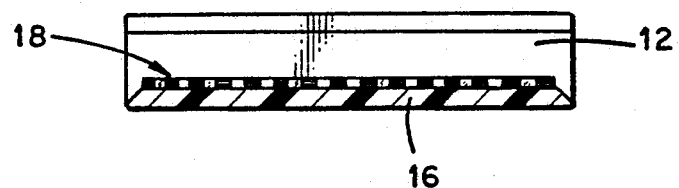
FIG. 4 is a sectional view of the gel tray depicted in FIG. 2 and taken along the line 4—4 of FIG. 2.

Referring now to FIG. 3, there is depicted a gel tray 10 for use in one embodiment of the present invention. The gel tray 10 is generally rectangular in shape with a first side wall 12 and a second side wall 14 on opposed sides of a generally rectangular base 16. The side walls 12 and 14 rise at right angles from the bottom of the base 16 to a height at least about 2 mm above the top of the base 16. Also, the side walls 12 and 14 traverse the length of opposite sides of the base 16. The two ends of the base 16 which are not attached to the sidewalls 12 and 14 are open and beveled to an angle of about 45°. A liquid crystal thermometer 18 is placed atop the base 16. A side view of the gel tray 10, through 4—4, is shown in FIG. 4.

There is shown in FIG. 5 a perspective drawing of a gel block 20 that is associated with the gel tray 10. The gel block 20 may be formed by pouring a gel solution, such as an agarose gel which is well known in the art, onto the gel tray 10 and allowing it to harden, or it may be pre-formed, stored and then placed onto the gel tray 10. The gel block 20 is generally rectangular in shape with a length from the first end 22 to a second end 24, a width from a first side 26 to a second side 28 and a depth from a first surface 30 to a second surface 32. The first surface 30 is generally flat. The depth of the gel block 20 does not substantially vary when going across the width from the first side 26 to the second side 28. The depth does vary when going from the first end 22 to the second end 24. The depth of the gel block 20 decreases in a substantially smooth manner at about a 45 degree angle from a maximum depth at the first end 22 to a minimum depth at a first point 34 along the length of the block 20. The depth of the block 20 does not vary substantially from the first point 34 along the length of the block to a second point 36 along the length of the block. The depth of the block 20 in the depicted embodiment then increases substantially smoothly at about a 45 degree angle from the second point 36 to the maximum depth at the second end 24 of the gel block 20. The gel block 20 thus formed may be generally divided into a first wedge section 38 between the first end 22 and the first point 34, a flat middle section 40 of substantially uniform cross-sectional area between the first point 34 and the second point 36 and a second wedge section 42 between the second point 36 and the second end 24. When the gel block 20 is formed, the flat middle section 40 is formed at a depth of no more than about 2 mm. Whereas the angle which establishes the transition in thickness of the gel block is depicted as about 45°, lesser or greater angles may be employed. It is preferred however that abrupt changes in thickness be avoided inasmuch as the intent is to establish an uninterrupted flow path for electrical current through the gel block while still providing the relatively enlarged possible contact area between the end of the gel block and its adjacent buffer solution.

The gel block 20 is formed with sample wells 44 for receiving a sample solution. The preferred sample wells 44 are formed with a generally triangular cross-section when viewed at right angles to the first surface 30 with the apex of the triangle generally pointing in the expected direction of migration of the major components in the sample solution. The sample wells 44 are formed in the flat middle section 40 near the first point 34 of the gel block 20. There is shown in FIG. 6 a cross section of the gel block 20 as seen through 6—6 of FIG. 5.

There is shown in FIG. 7 a cross-section view of the gel tray 10 as seen through 7—7 of FIG. 3. In the depicted embodiment, the liquid crystal thermometer 18 is stabilized with respect to the base 16 and the side walls 12 and 14 of the gel tray 10 by the application of a suitable sealant 46, e.g. silicone caulk, to the side walls 12 and 14 and the thermometer 18. The depicted thermometer 18 is further divided into a first liquid crystal thermometer 48 and a second liquid crystal thermometer 50 mounted one atop the other. Between the thermometers 48 and 50 is placed a grid device 52. The grid device 52 is composed of a transparent plastic sheet upon which is marked an opaque grid. The temperature range of the first liquid crystal thermometer 48 is of a first temperature range (e.g. 0° to 20° C.) and the second liquid crystal thermometer 50 operates over a second temperature range (e.g. 20° to 40° C.). When the thermometers 48, 50 are at a temperature in the first temperature range, the thermometer 48 will be visible through the grid 52. In other words, the grid of the grid device 52 will be seen between 0° C. and 20° C. At the temperature in the second temperature range only the thermometer 50 will be seen. The grid device 52 will not be visible at, for example, 40° C. In this way the liquid crystal thermometer 18 may be used to measure a wider range of temperatures than may be possible with a single liquid crystal thermometer. Alternatively, a smaller temperature range may be monitored but with a higher precision for each of the individual thermometers 48 and 50. Prior to a preferred use of the gel tray 10 with the thermometer 18, a thin, transparent plastic sheet 54 is placed over the liquid crystal thermometer 18 and secured with a sealant 46. This protects the thermometer 18 from direct contact but allows thermal contact with the gel block 20.

Figure 11:
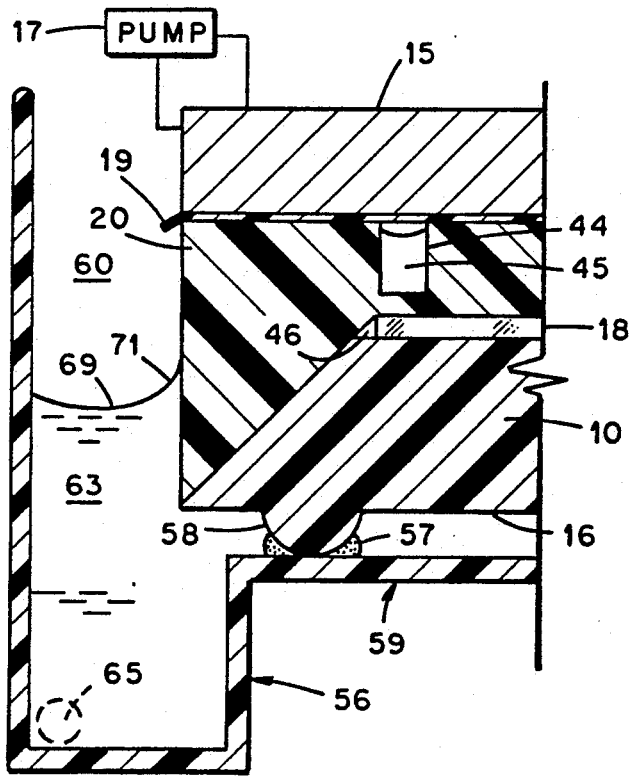
FIG. 11 is a partial view as in FIG. 10 and showing an alternative embodiment for sealing the gel tray to the pedestal.

When the gel block 20 is mounted in the gel tray 10, the entire assembly is then placed into a gel box 56, shown in FIG. 8. In the depicted embodiment, a sealant such as vacuum grease is shown as being applied to ridges 58 of pedestal 59 before the gel tray 10 is placed into the gel box 56. Alternatively, the ridges 58 may be a part of the gel tray 10 as depicted in FIG. 11. The distance between the ridges 58 is just sufficient to develop an electrically insulating space between the ridges and the gel tray and pedestal. Preferably, the ridges are spaced apart sufficiently as provides balanced support for the gel tray. Whereas there is depicted in the FIGURES the use of a sealant (e.g. vacuum grease) for ensuring that the buffer solution does not migrate past the juncture of the ridges 58 with the gel tray 10 (or vice versa as depicted in FIG. 11), it is to be recognized that the rounded distal surface of the ridge is selected to develop sufficiently intimate linear contact between the ridge and the gel tray such that the combination of the geometry of the ridge, its proximity to the gel tray and the surface tension of the buffer solution perform in the nature of a seal that prevents the migration, i.e. flow, of buffer solution therepast without the use of a sealant material.

Figure 1:
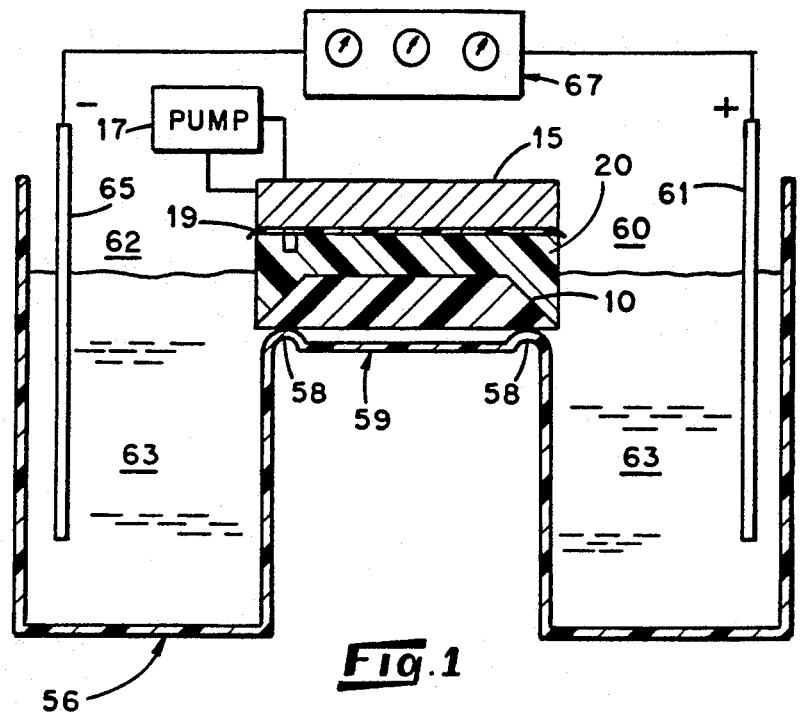
FIG. 1 is a schematic representation of a gel electrophoresis apparatus embodying various features of the present invention.
Figure 10:
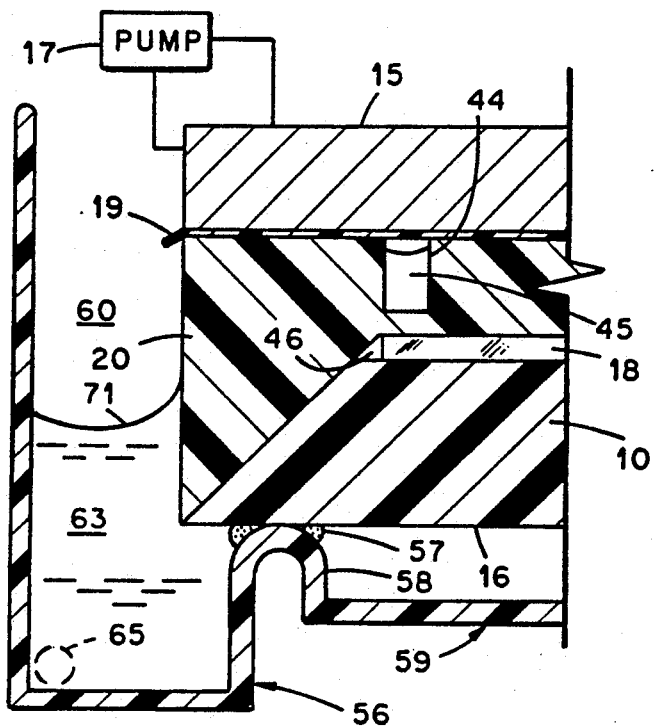
FIG. 10 is a partial view showing one corner of a gel block mounted in a gel tray, which in turn is mounted on a pedestal of a gel box in accordance with one embodiment of the present invention.

Immediately adjacent to and outside of each of the ridges 58 there are provided buffer wells, e.g. a cathode buffer well 60 on one side of the gel box 56 and an anode buffer well 62 on the other side of the gel box 56. Cathode and anode electrodes, 61 and 65, respectively (FIG. 1) are placed into the appropriate buffer well through electrode ports 64 or otherwise mounted with at least their distal ends being in contact with buffer solutions 63 in the buffer wells. After the electrodes have been placed into the appropriate buffer wells 60, 62 and the gel tray 10 has been mounted on the ridges 58, appropriate buffer solutions are loaded into the buffer wells 60 and 62 until the buffer solution in each well is in contact with the respective end of the gel block 20. As seen in FIGS. 1 and 10 in a preferred embodiment, the surface level 71 of the buffer solution 63 is at a level about midway of the thickness dimension of the end of the gel block. At this location of the buffer level, there is established good electrical contact between the buffer and the gel block, but there is no flow of buffer onto or over the surface 30 of the gel block. The ridges 58 act as dams to prevent the development of an electrically conductive path between the two buffer solutions by reason of buffer flowing from one well to the other. In preparation for the desired separation, the sample solutions are placed into the sample wells 44 of the gel block 20. A voltage is then applied between the cathode and the anode. By reason of the electrical path developed from the anode to the first buffer, to the gel block, to the second buffer, thence to the cathode, there is created a voltage across the gel block 20. This electrical potential causes the various charged components of the sample solution to begin to migrate through the gel block 20. After an appropriate period of time, the voltage is removed, the gel tray 10 is dismounted from the gel box 56 and the gel block 20 is examined for the individual components of the sample solution.

There is shown in FIG. 10 a cross-sectional view of a fragmentary portion of a preferred embodiment of the invention. FIG. 10 shows an apparatus with ridges 58 as a part of the pedestal 59 of the gel box 56. The gel tray 10 with the gel block 20 is then placed onto the ridges 58. As noted hereinabove, the ridges form seals between the base 16 of the gel tray 10 and the ridges 58 of the pedestal 59 of the gel box 56 and aid in defining an electrically insulating air space therebetween. A buffer solution 63 is then loaded carefully into the buffer well 60 or 62. The level of the buffer solution 63 is raised until it reaches the halfway mark up the end of the gel block 20. The seal between the gel tray 10 and the gel box 56 prevents the buffer solution 63 in one buffer well 60 or 62 from coming in contact with the buffer solution 63 in the other buffer well 62 or 60. The level of the buffer solution 63 is not raised to a point where it will submerge the gel block 20. FIG. 11 shows a similar apparatus with the ridges 58 on the gel tray 10 instead of on the pedestal 59 of the gel box 56. The seal between the tray 10 and the gel box 56 operates in a manner similar to the seal shown in FIG. 10.

As noted hereinbefore, the present inventor provides for maximum voltage development across the gel block by limiting the current flow path between the electrodes (and their respective buffer solutions) to flow through the gel block. In addition, in accordance with a further feature of the present invention, the ionic strength of the gel block is established at a value lower than the ionic strength of the buffer solutions. Preferably, the ionic strength of the buffer solutions are essentially the same. Such relatively lower ionic strength of the gel block causes the gel block to exhibit a higher electrical resistivity than the buffer solutions so that a greater proportion of the total voltage drop between the cathode and the anode is expressed across the gel block, as opposed to being expressed across each of the buffer solutions. In the examples recited hereinafter, it is to be noted that the preferred gel block includes about 1/5 as much TBE (buffer solution) as does the buffer solution.

There is shown in FIG. 12 a representation demonstrating the improved resolution of the desired separation(s) employing triangular sample wells over rectangular sample wells. A sample solution comprised of two components, A and B was placed in two different sample wells. Rectangular sample well 66 is of the type used in the prior art and triangular sample well 68 is an embodiment of one aspect of the present invention. A voltage was applied across a gel block into which these sample wells 66 and 68 had been formed. This voltage caused the components, A and B, to migrate through the gel block. After a period of time component A, which migrated more rapidly through the gel block, migrated to a first position 70; the B component of the sample solution had migrated to a second position 72. The sample solution placed into the rectangular well 66 had not been well separated as is shown by the overlap 74 between the trailing edge of component A overlapping with the leading edge of component B. The sample solution placed in the triangular sample well 68 had much better resolution as is shown by the small area of overlap 76 between the trailing edge of component A and the leading edge of component B. This improvement in resolution or ability to separate individual components is far superior to the separation achieved using the prior art as represented by the sample well 66.

A practical example of this improved resolution is shown in FIG. 13 which is representation of the result of a gel electrophoresis separation of Hind III cut lambda DNA. The sample solution was loaded into the sample wells at the starting position 78. A voltage gradient was applied across the gel block and the components of the sample solution migrated through the gel block. The voltage gradient was applied for 60 minutes. At the end of that time, the gel was removed and stained with ethidium bromide in doubly distilled water for 10 minutes. It may be seen that the components at positions 80 and 82 were well separated in the lane using the triangular sample well 84. The same components at positions 80 and 82 which originated from the rectangular well 86 were not well resolved.

There is shown in FIG. 13 a representation of the result of a gel electrophoresis separation of supercoiled plasmid DNA (pMK108) from other DNAs and RNAs present in a crude plasmid preparation using one embodiment of the present invention. This separation was completed over a period of 4 minutes. The crude plasmid preparation was loaded into the triangular sample well 88 and the voltage was applied across the gel block. At the end of 4 minutes the voltage was turned off, the gel block was removed and the gel block was stained. The various components of the crude plasmid preparation may be seen in FIG. 14: the desired supercoiled plasmid DNA is at position 90; chromosomal DNA is seen at position 92; nicked plasmid DNA is seen at position 94; and the cellular RNA is seen at position 96. The separation shown in FIG. 14 was not possible using the prior art gel electrophoretic techniques for 4 minutes or less.

It may be seen from the foregoing detailed description that the present invention does provide a dramatic improvement over the prior art techniques of separation of biological components.

In order to provide a better understanding of the present invention, the following example is provided to show an exemplary, non-limiting application.

EXAMPLE

Buffers

Water was double distilled or from MilliQ apparatus. All solutions were made and checked by pH and by conductivity. The solutions were: Buffer A (10 mM TrisCl, pH 8.3, 0.4 M NaCl, 1 mM EDTA), TBE (89 mM Tris base, 89 mM Boric Acid, 2 mM $NA_2EDTA$, pH 8.3, 1.07±0.02 mmho), 5xTBE(445 mM Tris base, 445 mM Boric Acid, 10 mM $NA_2EDTA$, pH 8.3, 3.62±0.02 mmho), TE(10 mM TrisCl, pH 8.0, 1mM EDTA, 0.96 mmho).

DNA Preparation

The plasmid, pMK108, was isolated from E. coli strain MK108 by an alkali lysis method through the isopropanol precipitation (Maniatis et al.; *Molecular Cloning*, Cold Spring Harbor Press, Cold Spring Harbor, N.Y.:1982) with the following modifications. Cell pellets were created in a JA-14 rotor for 10 minutes at 5000 rpm and 4° C. Cellular debris and chromosomal DNA were centrifuged in a JA-20 rotor for 80 minutes at 10,000 rpm and 4° C. Plasmid DNA was pelleted in a JA-20 rotor for 30 minutes at 10,000 rpm and 4° C. It was then washed with 70% ethanol, dried and resuspended in TE or in Buffer A. DNA purity and concentration were determined by UV spectroscopy on a Varian 2200 and by agarose gel electrophoresis. DNA stocks were 85 ng/μl to 1 μg/μl.

Gel Preparation

Fifteen mls of 0.65% agarose in TBE were melted and poured evenly into a gel tray. In the final design, wells were equilateral triangles (0.5 mm$^2$) with a vertex pointing away from the first end 22 (FIG. 4) of the gel. In the 1.5 to 3.0 mm thick gels each well would hold between 2.5 to 4.0 μl. The solidified gel was tightly covered with plastic wrap and cooled at least 30 minutes at 4° C. Just prior to use the gel was put in a −20° C. freezer for 3–4 minutes. A few ice crystals may form on the exposed surface of the gel. Gels penetrated by ice crystals were discarded.

Gel Running

Running buffer was 5xTBE. Samples (DNA solutions mixed 3:1 (v/v) with glycerol) were stored on ice. The gel tray was sealed to the apparatus with silicone high vacuum grease. Running buffer was added until it was level with the bottom of the gel tray. Wells were loaded with 2.0–2.5 μl of the sample using a rounded PAGE gel pipet tip. The gel was covered with high density polyethylene that extended 4 cm beyond all sides of the gel. The plastic at the ends of the gel was supported with 1 mm diameter glass rods. A 3 mm thick smoothed aluminum plate (−20° C.) was placed on the polyethylene. Two plastic bags of ice water were placed on the aluminum. Excellent thermal contact between all layers was essential. The buffer level was increased to complete the electrical circuit but not to the top of the gel.

Electrophoresis

An EC 600 power supply was used in voltage limiting mode with 150 mA and 150 W backup limits. Timing began when the desired voltage (usually 350 V) was reached. Voltage, amperage, and wattage were closely monitored and were recorded at one minute intervals.

Staining and Photography of the Gels

Gels were stained with 0.5 µg/ml EtdBr and then destained in double distilled H$_2$O to remove excess EtdBr. The gels were illuminated by a transilluminator and photographed with a Polaroid MP-4 camera using Polaroid 107 film.

Results

The results of the separation for a time period of four minutes are shown in FIG. 14. The supercoiled plasmid DNA is shown at position 90. The other components of the preparation are also shown (chromosomal DNA 92, nicked plasmid DNA 94 and cellular RNA 96). The samples were loaded into triangular sample wells 88.

It will be recognized from the foregoing that the present invention provides a method and apparatus for rapidly and efficiently separating the components of a sample solution using elevated voltages for periods of time substantially less than required in the techniques of the prior art. The present invention also provides a means for monitoring the temperature of the supporting medium.

Various of the features of the invention which are believed to be novel are set forth in the appended claims.

What is claimed is:

1. A method for the separation of components of a sample solution employing gel electrophoresis, said components being degradable or denaturable at temperatures substantially above room temperature, the method including the steps of:
   disposing said sample solution in a well formed in a gel block having a maximum thickness in the sample-containing area thereof of less than about 2 mm, such well having a generally triangular cross section when viewed perpendicularly to the path of electrical current flow through the gel block;
   positioning said gel block between first and second buffer solutions with the opposite extremities in the gel block in electrical contact with the buffer solutions such that there is developed an electrically conductive path through the gel block and between the buffer solutions;
   passing electrical current through the gel block via the buffer solutions, said electrical current having a voltage component of between about 30 and 120 volts per centimeter of the length of the gel block wherein said voltage component is applied for a time period between about the limits given by the following equations:

$E = 0.5 t^{1.1}$, $E = 500 t^{-1}$, and $E = 500 t^{-0.1}$, wherein

E is the voltage component in volts across the gel block and t is the time period in hours, whereby each of said components move different distances through the gel block based on the charge of each of said components, the size of each of said components and the amount of electrical current through the gel block; and
   withdrawing heat from said gel block at a rete sufficient to maintain said gel block in a substantially solid state under the conditions of applied voltage and time and to maintain said sample at a temperature below that at which the separable components thereof materially degrade or denature.

2. A method for the separation of nucleic acids and their complexes in a sample solution employing gel electrophoresis, the method including the steps of:
   disposing said sample solution in a gel block having a maximum thickness in the sample-containing area thereof of less than about 2 mm;
   positioning said gel block between first and second buffer solutions with the opposite extremities of the gel block in electrical contact with the buffer solutions such that there is developed an electrically conductive path through the gel block and between the buffer solutions;
   passing electrical current through the gel block via the buffer solutions, said electrical current having a voltage component of between about 30 and 120 volts per centimeter of the length of the gel block wherein said voltage component is applied for a time period between about the limits given by the following equations:

$E = 5.5 t^{1.1}$, $E = 500 t^{-1}$ and $E = 500 t^{-0.1}$, wherein

E is the voltage component in volts across the gel block and t is the time period in hours, whereby each of said nucleic acids and their complexes moves different distances through the gel block based on the charge of each of said components, the size of each of said components and the amount of electrical current through the gel block; and
   withdrawing heat from said gel block at a rate sufficient to maintain said gel block in a substantially solid state under the conditions of applied voltage and time and to maintain said sample at a temperature below that which the nucleic acids and their complexes materially degrade or denature.

3. The method of claim 2 characterized in that the gel block is maintained at a temperature not exceeding its melting point during that period of time when an electrical current is flowing therethrough.

4. The method of claim 2 and further characterized in that the ionic strength of said gel block is substantially less than the ionic strength of said buffer solution whereby the voltage drop across said gel block is greater than the voltage drop across the buffer solution between an electrode and the gel block.

5. A method for the separation of components of a sample solution employing gel electrophoresis, said components being degradable or denaturable at temperatures substantially above room temperature, the method including the steps of:

disposing said sample solution having a maximum thickness in the sample-containing area thereof of less than about 2 mm;

positioning said gel block between first and second buffer solutions with the opposite extremities of the gel block in electrical contact with the buffer solutions such that there is developed an electrically conductive path through the gel block and between the buffer solutions;

passing electrical current through the gel block via the buffer solutions, said electrical current having a voltage component of between about 30 and 120 volts per centimeter of the length of the gel block wherein said voltage component is applied for a time period between about the limits given by the following equations:

$E = 0.5 t^{1.1}$, $E = 500 t^{-1}$, and $E = 500 t^{-0.1}$, wherein

E is the voltage component in volts across the gel block and t is the time period in hours, whereby each of said components move different distances through the gel block based on the charge of each of said components, the size of leach of said components and the amount of electrical current through the gel block;

placing a liquid crystal thermometer in thermal transfer relationship with the gel bock and removed from contact with the buffer solutions;

monitoring at least one temperature of the gel block with the liquid crystal thermometer at least before and after separating the components of the sample solution; and withdrawing heat from said gel block at a rate sufficient to maintain said gel block in a substantially solid state under the conditions of applied voltage and time and to maintain said sample at a temperature below that at which the separable components thereof materially degrade or denature.

6. A method for the separation of components of a sample solution employing gel electrophoresis comprising disposing the sample solution in a well of a gel block, said well having a triangular cross-section when viewed perpendicularly to the path of current flow through the block, positioning the block between first and second buffer solutions with the opposite extremities of the gel block in electrical contact with the buffer solutions such that there is developed an electrically conductive path through the gel block and between the buffer solutions, and passing electrical current through the gel block via said buffer solutions whereby the separatable components of said sample solution travel along the gel block in substantially triangular groupings as viewed from an angle that is substantially at right angles to a surface of the gel block.

7. A preformed gel block for use in a gel electrophoresis apparatus wherein the gel block has a generally rectangular shape with a length from a first end to a second end, a width from a first side to a second side and a depth from a substantially flat first surface to a second surface and the block has sample wells for accepting the sample solution, characterized in that the depth of the gel block (a) does not substantially vary across its width at right angles to the length of the block and the depth of the block, (b) decreases substantially smoothly from a first maximum at the first end of the block to a minimum at a first point along the length of the block, (c) does not vary substantially from the minimum at the first point along the length of the block to the minimum at a second point along the length of the block, (d) increases substantially smoothly from the minimum at the second point along the length of the block to a second maximum at the second end of the block, and (e) between the first point and the second point is of a magnitude whereby there is an efficient heat transfer out of the block when the apparatus is in use, and, the sample wells have a substantially triangular cross-sectional geometry when viewed perpendicularly to the direction of the path of the current flowing through the gel block, whereby the separation of the components of the sample is facilitated.

8. The gel block of claim 7 characterized in that the gel block is an agarose gel block.

9. The gel block of claim 8 characterized in that the depth of the preformed gel block between the first point along the length of the block and the second point along the length of the block is less than 2 millimeters.

10. The gel block of claim 7 characterized in that the first maximum depth equals the second maximum depth.

11. A gel electrophoresis apparatus for separating components of a sample solution including a gel block with at least one sample well for receiving said sample solution, a gel tray for holding the gel block and a gel box for holding at least two quantities of buffer solution and for holding the gel block in contact with the buffer solutions characterized in that a liquid crystal thermometer is placed between and in thermal contact with the gel block and the gel tray whereby the temperature of the gel block may be monitored at least before and after operation of the apparatus.

12. The apparatus of claim 11 characterized in that the liquid crystal thermometer further comprises a plurality of liquid crystal thermometers, each of the plurality indicating a temperature range of a plurality of temperature ranges, and, there is provided means for distinguishing the indication of each of the plurality of said liquid crystal thermometers from the indication of other, whereby the temperature of the gel block may be monitored over a range of temperatures including the plurality of temperature ranges.

13. The apparatus of claim 12 characterized in that the means from distinguishing the indication of each of the plurality of liquid crystal thermometers comprises at least one indicator mounted between at least two of the plurality of liquid crystal thermometers whereby said indicator is visible when the gel block is at a temperature within the temperature range of one of the at least two of the plurality of liquid crystal thermometers and said indicator is not visible when the gel block is at a temperature within the temperature range of the other of said plurality of liquid crystal thermometers.

14. The apparatus of claim 13 characterized in that the indicator is a non-transparent grid on a transparent sheet.

15. A gel block for use in a gel electrophoresis apparatus for separating components of a sample characterized in that said gel block includes opposite ends and a length dimension defined between said ends, said length dimension being substantially parallel to the path of current flow through the block and that said gel block includes at least one sample well that has a substantially triangular cross-section when viewed perpendicularly to said length dimension.

16. The gel block of claim 15 characterized in that said triangular cross-section defines an isosceles triangle.

17. The gel block of claim 15 characterized in that the sample well is oriented with respect to the length of said gel block such that one apex of its triangular geometry is oriented substantially parallel to said length dimension and in the direction of anticipated migration of at least a selected one of the components of the sample when subjected to an electrical current flowing through the gel block.

* * * * *